United States Patent
Natu et al.

(10) Patent No.: US 11,571,387 B2
(45) Date of Patent: Feb. 7, 2023

(54) PROCESS FOR THE PREPARATION OF POWDERED PROBIOTIC FORMULATIONS FOR MONOGASTRIC ANIMALS

(71) Applicant: PRAJ INDUSTRIES LIMITED, Pune (IN)

(72) Inventors: Aamod Anil Natu, Hinjewadi (IN); Sharad Krishnachandra Laldas, Hinjewadi (IN); Shaileshkumar Dhondiram Sawale, Hinjewadi (IN); Shilpa Sachin Pradhan, Hinjewadi (IN); Aarohi Atul Kulkarni, Hinjewadi (IN)

(73) Assignee: PRAJ INDUSTRIES LIMITED, Pune (IN)

( * ) Notice: Subject to any disclaimer, the term of this patent is extended or adjusted under 35 U.S.C. 154(b) by 221 days.

(21) Appl. No.: 16/484,971

(22) PCT Filed: Mar. 5, 2018

(86) PCT No.: PCT/IN2018/050116
§ 371 (c)(1),
(2) Date: Aug. 9, 2019

(87) PCT Pub. No.: WO2018/179001
PCT Pub. Date: Oct. 4, 2018

(65) Prior Publication Data
US 2020/0352860 A1 Nov. 12, 2020

(30) Foreign Application Priority Data
Mar. 27, 2017 (IN) .............................. 201710010721

(51) Int. Cl.
| | | |
|---|---|---|
| A61K 9/19 | (2006.01) |
| A61K 35/741 | (2015.01) |
| A61K 35/744 | (2015.01) |
| A23K 20/163 | (2016.01) |
| A23K 40/10 | (2016.01) |
| A23K 40/30 | (2016.01) |
| A23K 50/75 | (2016.01) |
| A23K 10/18 | (2016.01) |
| A61K 9/48 | (2006.01) |
| A61K 35/742 | (2015.01) |
| A61K 35/00 | (2006.01) |

(52) U.S. Cl.
CPC .............. *A61K 9/19* (2013.01); *A23K 10/18* (2016.05); *A23K 20/163* (2016.05); *A23K 40/10* (2016.05); *A23K 40/30* (2016.05); *A23K 50/75* (2016.05); *A61K 9/4866* (2013.01); *A61K 35/741* (2013.01); *A61K 35/742* (2013.01); *A61K 35/744* (2013.01); *A23Y 2320/25* (2013.01); *A61K 2035/115* (2013.01)

(58) Field of Classification Search
None
See application file for complete search history.

(56) References Cited

U.S. PATENT DOCUMENTS

| | | | |
|---|---|---|---|
| 7,427,397 B2 * | 9/2008 | Adams ................. | A61K 35/741 424/93.4 |
| 8,445,226 B2 * | 5/2013 | Garner ..................... | C12N 1/20 435/41 |
| 9,504,275 B2 * | 11/2016 | Harel .................... | A23K 20/147 |
| 2005/0266069 A1 | 12/2005 | Simmons et al. | |
| 2011/0008493 A1 | 1/2011 | Zorea | |
| 2014/0010918 A1 | 1/2014 | Quintens et al. | |

OTHER PUBLICATIONS

Cabri Laboratory Procedures for Microorganisms; Preservation of bacteria by freeze-drying. Dated Apr. 2013; pp. 1-2; retrieved on Jun. 4, 2021 from webpage www.cabri.org/guidelines/micro-organisms/M300Ap508.html.*
Shankar Ilango et al. J Food Sci Technol, Feb. 2016, 53(2), pp. 977-989.*
International Search Report and Written Opinion for PCT/IN2018/050116, dated May 30, 2018.
Martin MJ, et al., "Microencapsulation of bacteria: A review of different technologies and their impact on the probiotic affects", Innovative Food Science & Emerging Technologies, Feb. 1, 2015, vol. 27, pp. 15-25.
Ding WK, et al., "An improved method of microencapsulation of probiotic bacteria for their stability in acidic and bile conditions during storage", Journal of Food Science, Mar. 1, 2009, vol. 74, No. 2, https://doi.org/10.1111/j.1750-3841.2008.01030.x.

* cited by examiner

*Primary Examiner* — Vera Afremova
(74) *Attorney, Agent, or Firm* — Billion & Armitage

(57) ABSTRACT

The invention relates to a process for the preparation of dry lyophilized powdered formulations of probiotic bacteria for monogastric animal (for example poultry birds) using a combination of different polymers through the process of encapsulation. The resulting lyophilized powders of probiotic bacteria are having increased viability during animal feed processing, storage and upon transfer to the monogastric animal's digestive system.

9 Claims, 3 Drawing Sheets

PROCESS FOR THE PREPARATION OF POWDERED PROBIOTIC FORMULATIONS FOR MONOGASTRIC ANIMALS

FIELD OF THE INVENTION

The invention relates to a process for the preparation of dry lyophilized powdered formulations of probiotic bacteria for monogastric animal (for example poultry birds) using a combination of different polymers through the process of encapsulation. The resulting lyophilized powders of probiotic bacteria are having increased viability during animal feed processing, storage and upon transfer to the monogastric animal's digestive system.

BACKGROUND

The monogastric animals have a simple gastrointestinal system consisting of oesophagus, stomach, small intestine, large intestine, colon and rectum assisted with liver and pancreas in some cases. The pH of the stomach is about 1.5-2.0 causing it to be a highly acidic environment wherein survival of any microbe is a challenge. Post stomach the pH gradually changes from 2.0-7.0 in the small intestine whereas it becomes alkaline (8.5-9.0) in the colon. Generally in case of monogastric digestive systems, the challenges for effective delivery of probiotic bacteria are:
1. Acidic gastric environment affecting the viability and adequate number of viable cells from reaching and colonizing the small intestine which is the site of action.
2. Process difficulties especially heat treatment during feed blending, pelletization, etc. and
3. Logistics and shelf life issues of probiotic with respect to storage under differing conditions of temperature and moisture.

Since the probiotic bacteria are not tolerant to acidic environment in stomach and get killed instantaneously at low pH, thus reducing the effective probiotic microbe concentration required to enter the further parts of the system. Whether they are given through food or feed, they face harsh processing conditions mainly that of heat. Heat tolerance needs to be imparted as the majority of microbes cannot withstand high heat for extended time. With these technical hurdles, an additional commercial criterion is the need to survive exposure to harsh and varying physical and environmental conditions of formulation storage.

A method for protecting the probiotic microbe from these adverse conditions is protection in the form of encapsulation. For development of the encapsulation technology, *Bacillus amyloliquefaciens* and *Propionibacterium freudenrechii* were selected as probiotic strains; however, the technology disclosed herein is equally applicable on other organisms.

Encapsulation is one known method to increase the shelf life of probiotic formulations. Encapsulation is a process in which tiny droplets or particles are wrapped with a protective coating yielding capsules enclosing the bacteria. Encapsulation of these probiotic bacteria is generally used to maintain the viability during processing till the site of action in GI tract. It is critical for the targeted delivery of a minimum required cell count in GI tract. The probiotics are used with the animal feed, pharmaceutical products, and health supplements. They play a great role in maintaining gut health. As the survival of these bacteria in the digestive system is questionable so in order to protect the viability of the probiotic bacteria, several types of biopolymers such as alginate, chitosan, gelatin, whey protein isolate, pectin, cellulose derivatives have been used for the encapsulation and several methods of encapsulation such as spray drying, extrusion, emulsion have been reported.

The invention presented herein discloses a process for the preparation of powdered formulations of probiotic bacteria on a large scale using combination of two different polymers resulting in a material matrix that has a low porosity and that helps in lowering the exposure to unfavourable environmental conditions in the monogastric animal's gastro intestinal tract. These formulations are easy to handle and transport and more stable at ambient conditions.

BRIEF DESCRIPTION OF THE DRAWINGS

FIG. 2A is the spectrum of carboxymethyl cellulose sodium salt. FIG. 2B is the spectrum of maltodextrin. FIG. 2C is the spectrum of 0.5% CMC+1% maltodextrin mixture. FIG. 2D is the spectrum of 0.5% CMC+1% maltodextrin mixture enclosing the bacterial cells.

DETAILED DESCRIPTION

Figure 1A:
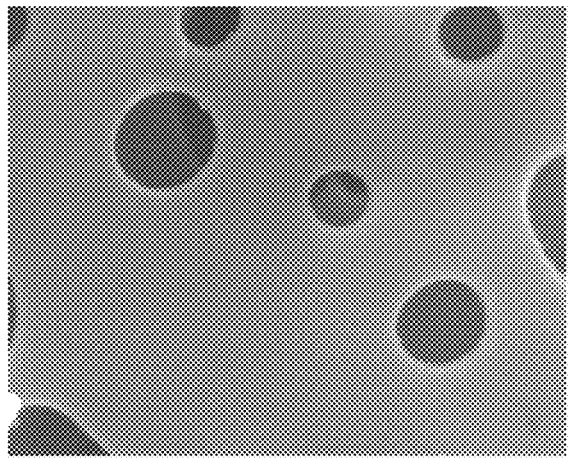
FIGS. 1A-D provide details of the SEM analyses of Example 6. A & B show the encapsulating agent as a powder and C & D show the encapsulating agent enclosing the bacterial cells forming particles of definite size and shape.
Figure 1B:
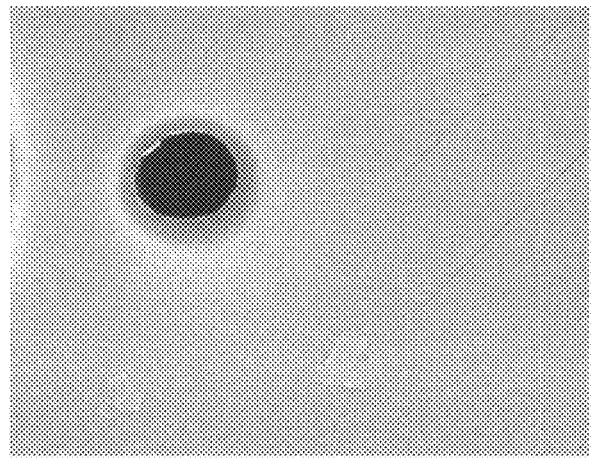
Figure 1C:
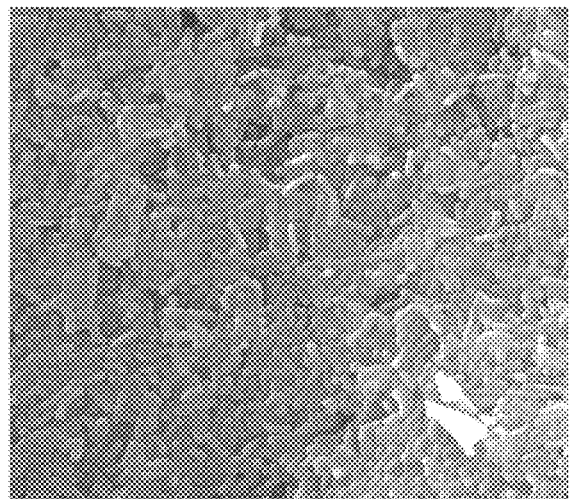
Figure 1D:
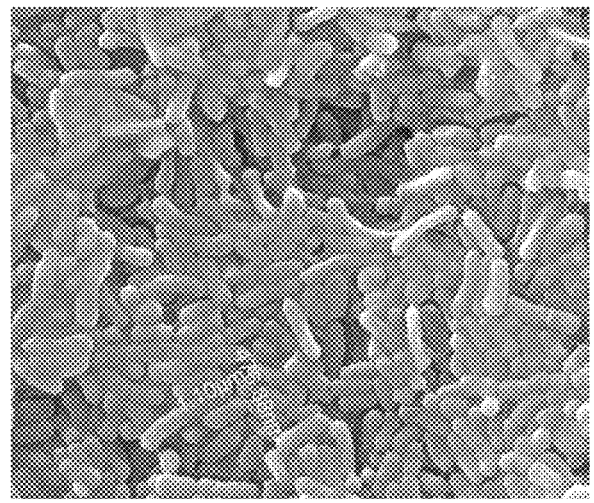

In one embodiment of the invention, for development of the encapsulation technology, *Bacillus amyloliquefaciens* and *Propionibacterium freudenrechii* were selected on the basis of their known probiotic properties.

In another embodiment of the invention, about 20-hour old or freshly grown probiotic cell biomass was used, unless otherwise stated. Different matrix polymers either individually or in combination were evaluated in the microencapsulation process.

Non-encapsulated cells served as the control for in comparative cases. The total viable count for *Propionibacterium freudenrechii* in MRS medium is about $2.98 \times 10^9$ CFU/ml in static incubation and for *Bacillus amyloliquefaciens* $7.80 \times 10^9$ CFU/ml under shaking incubation condition at 37° C. for about 24 hours using conical flasks of 1000 mL capacity. Said media is selected further for fermentation and for probiotic formulation development. Further said inoculum is inoculated in MRS broth and incubated at static condition for about 24 hours at about 37° C. Further, said broth is subjected to centrifugation with feed rate of about 500 ml/min to separate the wet cake. Next, the wet cake is immediately removed aseptically in LAF unit (Laminar Air Flow). Further about 0.5% carboxymethylcellulose (CMC) and about 1% of maltodextrin is used as an encapsulation agent. Such encapsulation solution is sterilized at about 121° C. for about 20 minutes. Further said wet cake and encapsulating chemicals (1% maltodextrin+0.5% CMC) are mixed properly using vortex mixer to prepare a lyoslurry. Then said prepared lyoslurry is poured in trays and subjected to freezing at about −80° C. for about 2 hours. Post freezing, the frozen lyoslurry is subjected to lyophilization at about −50° C. for about 28 to about 36 hours to prepare lyopowder. The lyopowder obtained is analyzed for TVC and solids contents. Said broth, wet cake, lyoslurry and lyopowder are serially diluted using sterile degassed saline Tween 80 solution and plated over sterile MRS agar plates. Said plates are incubated at about 37° C. for about 48 to about 72 hours. The total solid and TVC values for broth, wet cake, lyopowder and for lyoslurry are enlisted in TABLE A and B.

TABLE A

TVC of *Bacillus amyloliquefaciens* culture at different process stages

| No. | Sample | TS (% w/w) | TVC (CFU/gm) |
|---|---|---|---|
| 1 | Harvest/Broth | 2.71 | $1.7 \times 10^{10}$ |
| 2 | Wet cake | 14.86 | $2.6 \times 10^{10}$ |
| 3 | Lyoslurry | 6.52 | $4.1 \times 10^{13}$ |
| 4 | Lyopowder | 97.5 | $1.8 \times 10^{9}$ |

TABLE B

TVC of *Propionibacterium freudenreichii* culture at different process stages

| No. | Sample | TS (% w/w) | TVC (CFU/gm) |
|---|---|---|---|
| 1 | Harvest/Broth | 3.12 | $3.5 \times 10^{10}$ |
| 2 | Wet cake | 17.06 | $3.1 \times 10^{12}$ |
| 3 | Lyoslurry | 9.00 | $3.4 \times 10^{14}$ |
| 4 | Lyopowder | 96.1 | $2.3 \times 10^{14}$ |

In another embodiment of the invention, said lyopowder formulations are packed in air-tight containers and stored at room temperature at about 50% relative humidity. The moisture contents of lyopowder formulations are not more than 5% by weight. During storage after specified time periods the TVC analyses are carried out to check the viability of bacteria in the formulations.

In another embodiment of the invention, before the production of dry powders of probiotic, the probiotic cultures were selected on the basis of survival efficiency with respect to simulated harsh environmental conditions such as the exposure to high temperature and high bile salts concentration (gastric fluid) in stomach.

In another embodiment of the invention, the bacterial cultures were revived from the glycerol stock using nutrient broth for *Bacillus* and MRS broth for *Propionibacterium*. For this 250 µl of culture from glycerol stock was inoculated in 100 ml nutrient/MRS broth in 250 ml flask. The culture was incubated at 37° C., under shaking/static condition, for about 18±2 hours. From this 20 ml was taken in two 150 ml flask individually. One flask labeled as control flask, was diluted and plated on nutrient/MRS agar plate for total viable count (TVC) analysis. The second flask was treated at 90° C. for one minute in water bath. Dilution plating of the sample from both the flasks was done on nutrient/MRS agar medium for TVC determination. For dilution plating, 0.9 ml of Tween-saline (0.05% Tween 80+0.5% sodium chloride) was added in 2 ml Eppendorf tube, and 0.1 ml of culture was added to it to make $10^1$ dilutions and later serially diluted till $10^{12}$. From each dilution 0.1 ml was spread on nutrient agar and MRS agar plate respectively with the help of sterile L-spreader. Plates were incubated at 37° C. for 24 hours. Post incubation, growth was measured in terms of colony counts for every dilution plated and TVC was calculated using formula:—

TVC=(No. of colonies×dilution factor)/aliquot plated

Percent survival for the culture after heat treatment was calculated using formula:

% survival=(TVC after heat treatment)/(TVC before heat treatment)×10.

In next embodiment of the invention, the probiotic cultures to be tested were checked for tolerance to bile salts. Bile salt concentrations chosen for the assay were 0.5, 1.0, 1.5, 2 and 3%. The required amount of bile salt was mixed with nutrient (for *Bacillus*)/MRS broth (for *Propionibacterium*) and sterilized at 121° C. for 20 minutes. The sterilized broth was inoculated using 1 ml freshly grown and centrifuged media free cell suspension of bacteria to be tested. This was incubated at 37° C. for 24 hours under shaking/static condition. Growth was monitored visually and TVC was enumerated by dilution plating on agar medium. To verify the tolerance the growth of the culture was also tested on nutrient/MRS agar plate containing the required amount of bile salt by surface spreading.

In yet another embodiment of present invention, other polymers like 1% carboxy methyl cellulose sodium salt (CMC-Na), carboxy methyl cellulose sodium salt+maltodextrin (0.5% CMC+1% MD), 1% alginate, 1% kappa carrageenan, 1% gelatin and 1% pectin are also tested alone or in combination as encapsulating agents for probiotic bacteria for the preparation of the dry powders.

In yet another embodiment of present invention, the probiotic bacteria is one of *Bacillus amyloliquefaciens* or *Bacillus licheniformis* or *Bacillus subtilis* or *Bacillus coagulans* or *Propionibacterium freudenreichii* or *Pediococcus acidilactici* combination thereof.

Embodiments provided above give wider utility of the invention without any limitations as to the variations that may be appreciated by the person skilled in the art. A non-limiting summary of various embodiments is given above, which demonstrate the advantages and novel aspects of the process disclosed herein.

Advantages:
1. A unique encapsulation process helps in restricted release of probiotic microbe in the small intestine of monogastric digestive systems using a combination of polymers for better protection.
2. The probiotic cultures tested for encapsulation are already tolerance tested for bile salts, thermal treatment, and survival in simulated gastric and intestinal fluids.
3. Said encapsulation agents used have a low porosity thus contributing to less exposure of the probiotic microbes to environment.
4. The encapsulated dry formulations have increased bacterial viability during processing and application in the monogastric digestive system.
5. The probiotic dry product is more stable and easier for handling and transport.

Examples provided below give wider utility of the invention without any limitations as to the variations that may be appreciated by the person skilled in the art. A non-limiting summary of various experimental results is given in the examples, which demonstrate the advantages and novel aspects of the process for preparation of dry probiotic microbe formulations using combination of polymers in a unique microencapsulation technique.

Example 1

A strain of *Propionibacterium freudenreichii* (MTCC 1371) was used for the preparation of dry powdered formulations. Said bacteria was grown in deMan Rogosa Sharpe (MRS) broth medium in static incubation condition at about 37° C. for about 24 hours in conical flasks. The culture was routinely transferred and stored at about −80° C. in about 20% glycerol by volume between transfers. The total viable count in MRS medium was about $2.98 \times 10^9$ CFU/ml.

A strain of *Bacillus amyloliquefaciens* (MTCC 10456) was used for the preparation of dry powdered formulations.

Said bacteria was grown in nutrient broth or MRS broth medium in shaking incubation condition at about 37° C. for about 24 hours in conical flasks. The culture was routinely transferred and stored at about −80° C. in about 20% glycerol by volume between transfers. The total viable count in MRS medium was about $7.8 \times 10^9$ CFU/ml compared with the nutrient broth at about $5.7 \times 10^8$ CFU/ml.

Example 2: Thermotolerance & Bile Tolerance of the Formulated Bacteria

The bacterial cultures were revived from the glycerol stock using nutrient broth for *Bacillus* and MRS broth for *Propionibacterium*. For this 250l of culture from glycerol stock was inoculated in 100 ml nutrient/MRS broth in 250 ml flask. The culture was incubated at 37° C., under shaking/static condition, for about 18 hours. From this 20 ml was taken in two 150 ml flask individually. One flask labeled as control flask, was diluted and plated on nutrient/MRS agar plate for total viable count (TVC) analysis. The second flask was treated at 90° C. for one minute in water bath. Dilution plating of the sample from both the flasks was done on nutrient/MRS agar medium for TVC determination. For dilution plating, 0.9 ml of Tween-saline (0.05% Tween 80+0.5% sodium chloride) was added in 2 ml eppendorf tube, and 0.1 ml of culture was added to it to make $10^1$ dilutions and later serially diluted till $10^{12}$. From each dilution 0.1 ml was spread on nutrient agar or MRS agar plate with the help of sterile L-spreader. Plates were incubated at 37° C. for about 24 hours. Post incubation, growth was measured in terms of colony counts for every dilution and TVC was calculated. TABLE 3 shows the thermo tolerance of the bacteria in the formulation compared with plain culture.

TABLE 2

| Heat exposure (90° C. for 1 min) | % Survival | |
|---|---|---|
| | *Bacillus amyloliquefaciens* | *Propionibacterium freudenreichii* |
| Non encapsulated probiotic | 28.21% (original count - $7.80 \times 10^9$, count post heat treatment - $2.20 \times 10^9$ cfu/ml) | 2.34% (original count - $2.98 \times 10^9$, count post heat treatment - $7.0 \times 10^7$ cfu/ml) |
| Encapsulated probiotic | 86% (original count - $6.90 \times 10^9$, count post heat treatment - $5.93 \times 10^9$ cfu/ml) | 60% (original count - $1.62 \times 10^9$, count post heat treatment - $9.72 \times 10^8$ cfu/ml) |

Example 3

Here the probiotic bacteria were checked for tolerance to bile salts. Bile salt concentrations chosen for the assay were 0.5, 1.0, 1.5, 2 and 3%. The required amount of bile salt was mixed with nutrient (for *Bacillus*)/MRS broth (for *Propionibacterium*) and sterilized at 121° C. for 20 minutes. The sterilized broth was inoculated using 1 ml freshly grown and centrifuged media free cell suspension of bacteria to be tested. This was incubated at 37° C. for 24 hours under shaking/static condition. Growth was monitored visually and TVC was enumerated by dilution plating on agar medium. To verify the tolerance, the growth of the culture was also tested on nutrient/MRS agar plate containing the required amount of bile salt by surface spreading. TABLE 3A and TABLE 3B show the data related to tolerance of bacteria upon encapsulation.

TABLE 3A

| Bile salt Concentration (g %) | Non-encapsulated *Propionibacterium freudenreichii* (cfu/ml) | Encapsulated *Propionibacterium freudenreichii* (cfu/ml) |
|---|---|---|
| 0 | $4.00 \times 10^{12}$ | $2.9 \times 10^{13}$ |
| 0.5 | $3.80 \times 10^6$ | $3.5 \times 10^8$ |
| 1.0 | $4.20 \times 10^4$ | $3.1 \times 10^6$ |
| 1.5 | $3.90 \times 10^4$ | $2.6 \times 10^6$ |
| 2.0 | $3.30 \times 10^4$ | $4.9 \times 10^4$ |
| 3.0 | $2.40 \times 10^4$ | $1.19 \times 10^4$ |

TABLE 3B

| Bile salt Concentration (g %) | Non-encapsulated *Bacillus amyloliquefaciens* (cfu/ml) | Encapsulated *Bacillus amyloliquefaciens* (cfu/ml) |
|---|---|---|
| 0 | $2.10 \times 10^{15}$ | $3.5 \times 10^{14}$ |
| 0.5 | $6.70 \times 10^{13}$ | $5.1 \times 10^{13}$ |
| 1.0 | $3.10 \times 10^{12}$ | $1.1 \times 10^{13}$ |
| 1.5 | $1.0 \times 10^{11}$ | $2.1 \times 10^{11}$ |
| 2.0 | $2.8 \times 10^9$ | $3.1 \times 10^{10}$ |
| 3.0 | $1.6 \times 10^9$ | $1.8 \times 10^{10}$ |

Example 4

Both *Bacillus amyloliquefaciens* and *Propionibacterium freudenrechii* cultures were inoculated in MRS broth flasks and incubated in static condition at about 37° C. for about 24 hours to form a starting culture. Next this starting culture was inoculated in 1.5 L MRS broth and incubated for about 24 hours at about 37° C. Post incubation both the broths were subjected to centrifugation to separate the biomass. Polymers like 1% carboxymethylcellulose sodium salt (CMC-Na), carboxymethylcellulose sodium salt+maltodextrin (0.5% CMC+1% MD), 1% alginate, 1% kappa carrageenan, 1% gelatin and 1% pectin were tested as encapsulating agents for probiotic bacteria for the preparation of the dry powders. The stock solutions containing 1% concentration of the encapsulating agents were sterilized at about 121° C. for about 20 min. The biomass of both microbes obtained after centrifugation was mixed with sterile solutions of encapsulation agents in 1:1 proportion. Said mixture was mixed well using vortex mixer. Obtained lyoslurry was then subjected to freezing at about −80° C. for 2 hours. Post freezing, the frozen lyoslurry was subjected to lyophilization at about −50° C. for about 28 to 36 hours to prepare the lyopowder [powdered probiotic formulations]. Said lyopowder and lyoslurry were serially diluted using sterile saline Tween 80 solution and plated over sterile MRS agar plates. Said plates were incubated at about 37° C. for about 24 to about 72 hours according to the culture. Total viable counts analyses of said lyopowder and lyoslurry were carried out to check the encapsulation potential of polymers and loss of viability of probiotic cells after lyophilization. The total viable counts of non encapsulated and encapsulated probiotic bacteria after lyophilization (lyopowder) are given in TABLE 4.

TABLE 4

ENCAPSULATION AGENTS SCREENING ASSAY

| LYOPOWDER | TVC (CFU/gm) data for encapsulation materials used | | | |
|---|---|---|---|---|
| TVC Culture Identity | 1% CMC | 0.5% CMC + 1% MD | 1% Sodium Alginate | 1% Gelatin |
| Propionibacterium freudenreichii | $2.23 \times 10^{12}$ | $2.54 \times 10^{13}$ | $2.63 \times 10^{9}$ | $2.03 \times 10^{13}$ |
| Bacillus amyloliquefaciens | $3.89 \times 10^{12}$ | $3.45 \times 10^{14}$ | $3.53 \times 10^{8}$ | $1.15 \times 10^{10}$ |

The control (non-encapsulated) TVC for both cultures were
1. *Propionibacterium freudenrechii:* $1.16 \times 10^{14}$ CFU/ml
2. *Bacillus amyloliquefaciens:* $1.10 \times 10^{13}$ CFU/ml Example 5: Assay for the Release of Encapsulated Cells in Simulated Gastric and Intestinal Fluids To check the efficiency of release of the bacterial cells from encapsulating materials at desired pH, the tolerance and release of the cells of *Bacillus amyloliquefaciens* and *P. freudenrechii* encapsulated in 0.5% CMC+1% MD were studied in SGF [simulated gastric fluid] with release in SIF [simulated intestinal fluid]. The encapsulated bacteria were resistant to the low pH of SGF and survived it for up to 6 hours. Similarly the encapsulated bacteria were easily released in SIF at high pH. The obtained data is shown in the TABLE 65A and TABLE 5B.

TABLE 5A

ENCAPSULATION RELEASE EXPERIMENT IN SGF

| Time [h] | Bacillus amyloliquefaciens | | Propionibacterium freudenreichii | |
|---|---|---|---|---|
| | Non-encapsulated | Encapsulated | Non-encapsulated | Encapsulated |
| 0 | $7.1 \times 10^{6}$ | $7.8 \times 10^{7}$ | $2.3 \times 10^{5}$ | $8.6 \times 10^{7}$ |
| 2 | $7.1 \times 10^{6}$ | $7.8 \times 10^{6}$ | $6.0 \times 10^{4}$ | $6.0 \times 10^{7}$ |
| 4 | $2.14 \times 10^{6}$ | $6.8 \times 10^{6}$ | $2.5 \times 10^{4}$ | $1.9 \times 10^{7}$ |
| 6 | $1.8 \times 10^{6}$ | $7.0 \times 10^{6}$ | 0 | $2.1 \times 10^{7}$ |

TABLE 5B

ENCAPSULATION RELEASE EXPERIMENT IN SIF

| Time [h] | Bacillus amyloliquefaciens | | Propionibacterium freudenreichii | |
|---|---|---|---|---|
| | Non-encapsulated | Encapsulated | Non-encapsulated | Encapsulated |
| 0 | $1.1 \times 10^{8}$ | $6.5 \times 10^{6}$ | $1.4 \times 10^{10}$ | $1.1 \times 10^{11}$ |
| 2 | $3.5 \times 10^{8}$ | $5.9 \times 10^{6}$ | $2.17 \times 10^{9}$ | $1.42 \times 10^{11}$ |
| 4 | $2.1 \times 10^{8}$ | $7.1 \times 10^{6}$ | $9 \times 10^{9}$ | $3.3 \times 10^{10}$ |
| 6 | $4 \times 10^{8}$ | $6.9 \times 10^{6}$ | $2.3 \times 10^{9}$ | $2.1 \times 10^{10}$ |

Example 6: Analysis of Encapsulated Cells by Scanning Electron Microscopy

To establish the morphology of the particles of the dry lyophilized powders [formulations] of *Bacillus amyloliquefaciens* and *Propionibacterium freudenreichii* using the encapsulating agent [0.5% CMC+1% maltodextrin] as such and with the bacterial cells enclosed were analysed under a scanning electron microscope. The details of analysis are included below.

FIGS. 1 A & B shows the encapsulating agent as such as a powdery matter. FIGS. 1 C & D shows the encapsulating agent enclosing the bacterial cells of *Bacillus amyloliquefaciens* and *Propionibacterium freudenreichii* forming particles of definite size and shape, respectively.

Example 7: Infrared Spectral Analyses of Encapsulated Formulations

To establish the spectral properties of the particles of the dry lyophilized powders of *Bacillus amyloliquefaciens* and *Propionibacterium freudenreichii* with the encapsulation agent with or without bacteria, the samples were analysed by FT-IR spectrometry.

IR Spectroscopy: The culture inoculated into broth was incubated at 37° C. for 24 hr. The broth was centrifuged (8000 rpm, 10 min, 4° C.) to collect the cells. The cells were washed three times with saline (0.85% sodium chloride). The cells were again re-suspended in saline and centrifuged. The obtained cell pellet was pre-freezed at −80° C. for 2 hr and lyophilized to obtain powdered form using lyophilizer. All spectra were recorded using Spectrum100FT-IR spectrometer (PerkinElmer). At least 8 scans, between wave number region 4000 cm$^{-1}$ to 500 cm$^{-1}$ with spectral resolution of 4 cm$^{-1}$, were taken for average estimation.

Figure 2A:
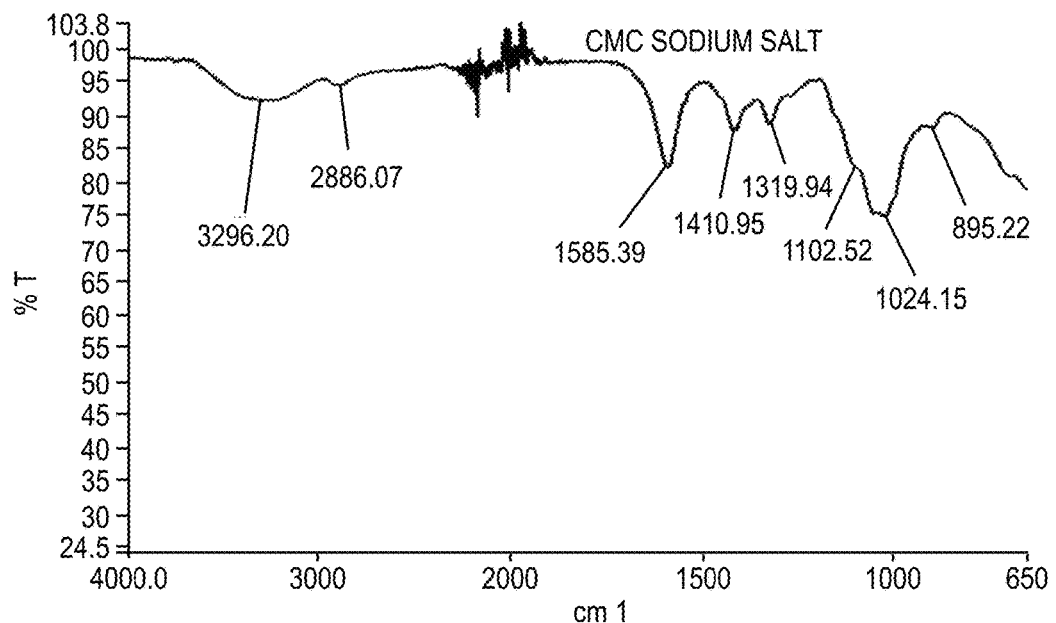
FIGS. 2A-D provide the details the FT-IR analyses of Example 7.
Figure 2B:
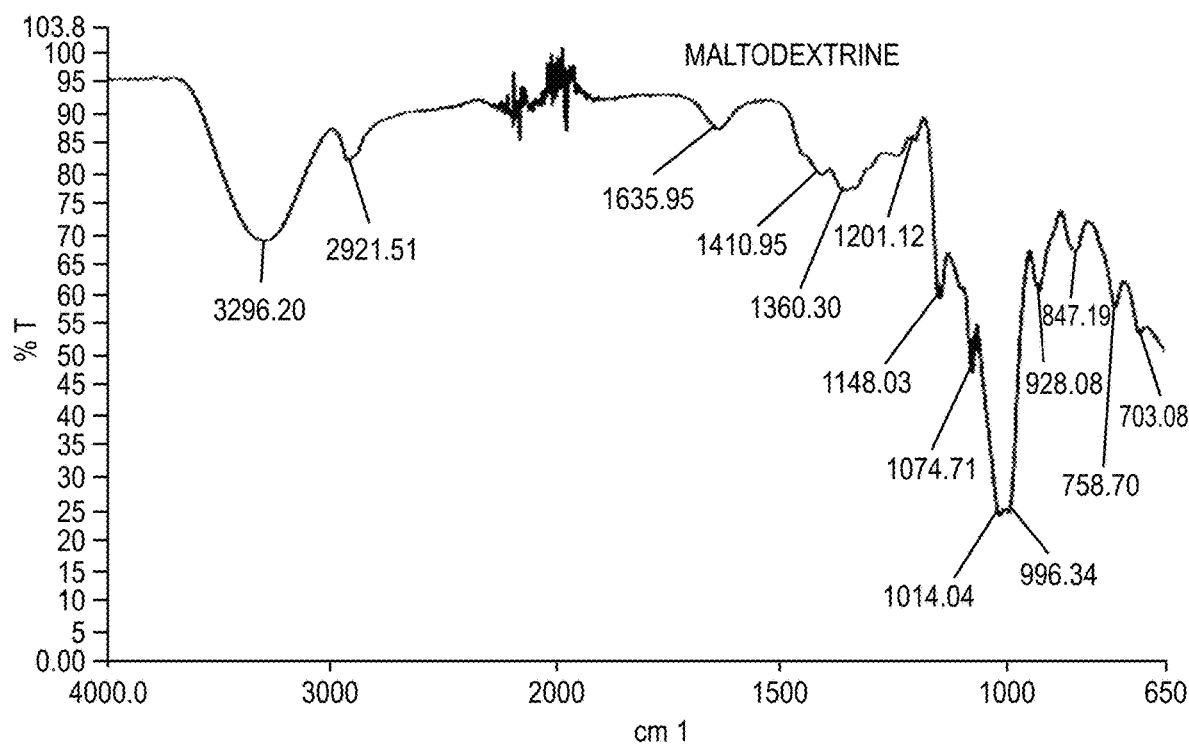
Figure 2C:
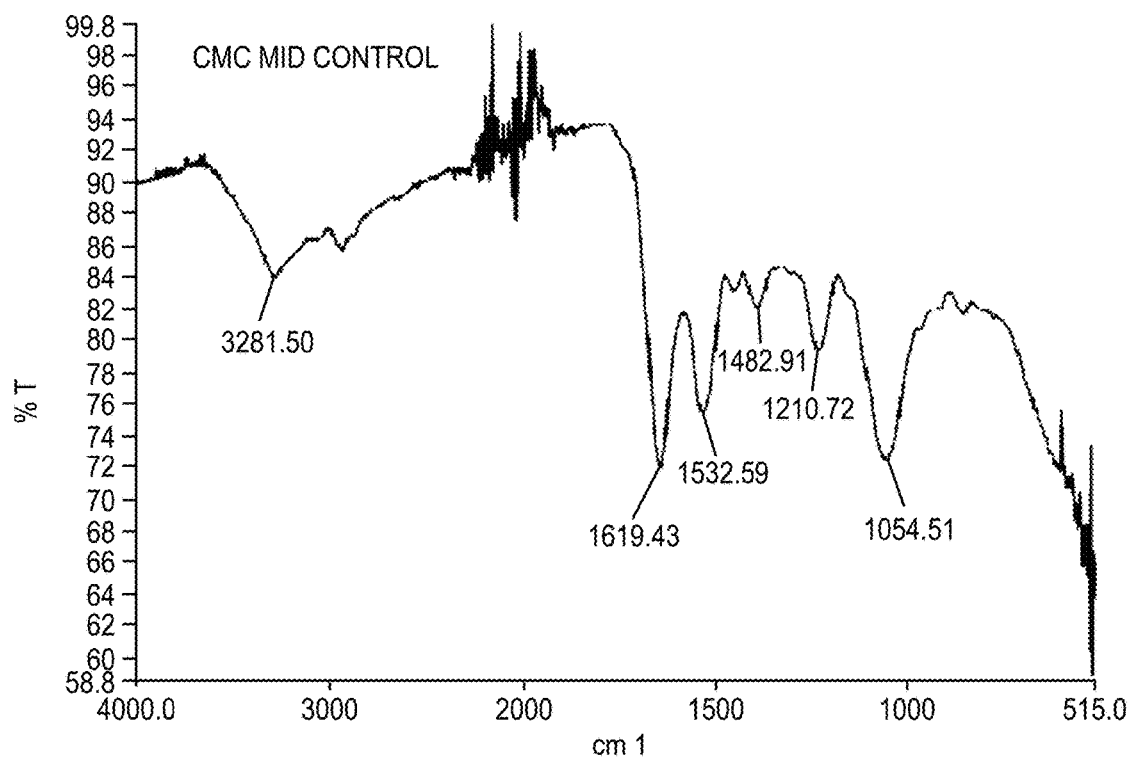
Figure 2D:
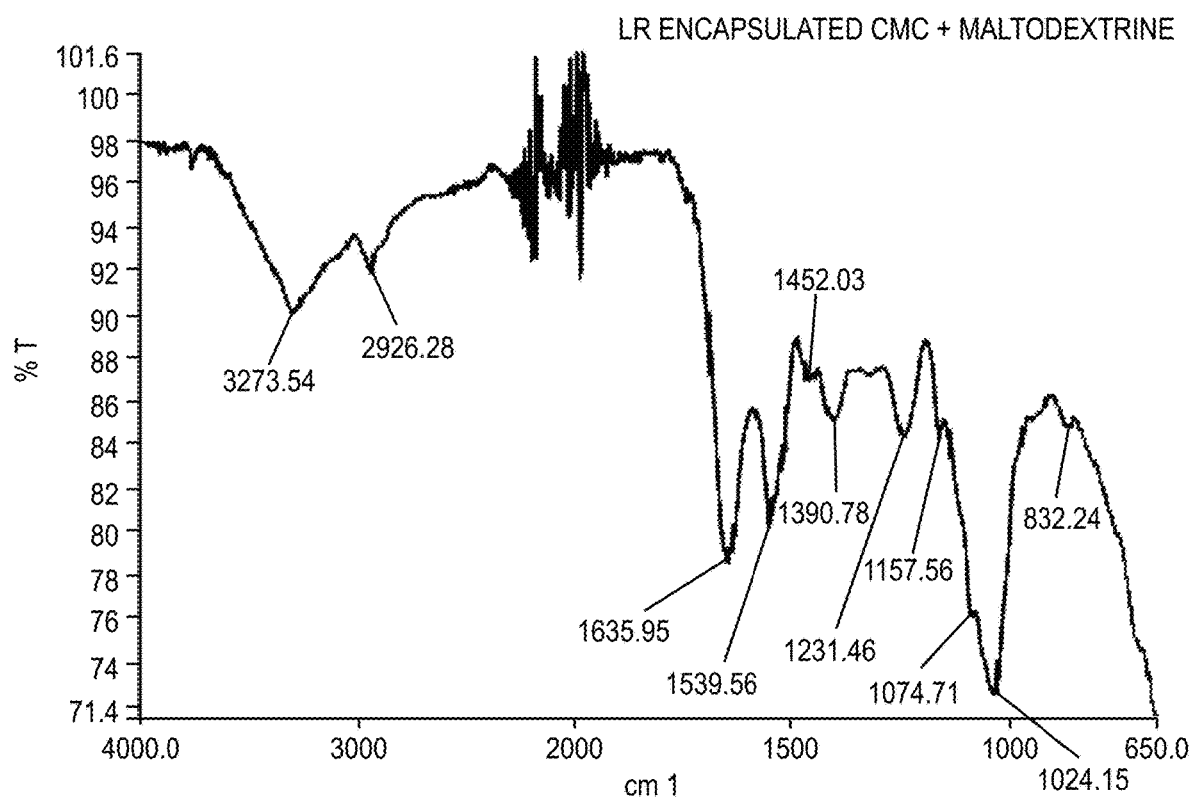

FIG. 2A is the spectrum of carboxymethyl cellulose sodium salt as such. FIG. 2B is the spectrum of maltodextrin as such. FIG. 2C is the spectrum of 0.5% CMC+1% maltodextrin mixture without bacterial cells. FIG. 2D is the spectrum of 0.5% CMC+1% maltodextrin mixture with bacterial cells. After mixing of both MD and CMC, absorption was not changed at major frequencies. However, after cell encapsulation, it exhibited new absorptions at about 1150 cm$^{-1}$ and 1453 cm$^{-1}$ which are remarkable for the encapsulated formulations of the bacteria herein in disclosed.

Embodiments provided above give wider utility of the invention without any limitations as to the variations that may be appreciated by the person skilled in the art. A non-limiting summary of various embodiments is given in the examples and tables, which demonstrate the advantageous and novel aspects of the process disclosed herein.

The invention claimed is:

1. A process for the preparation of a dry formulation of encapsulated probiotic bacteria comprising steps of:
   (a) providing a culture of *Bacillus amyloliquefaciens* or *Propionibacterium freudenreichii;*
   (b) subjecting said culture to centrifugation to separate bacteria as a wet cake;
   (c) mixing said wet cake with a solution to form a lyoslurry, wherein said solution consists essentially of about 0.5% by weight carboxymethyl cellulose sodium salt and about 1% by weight maltodextrin;
   (d) encapsulating the probiotic bacteria in the carboxymethyl cellulose sodium salt and maltodextrin of the solution by lyophilising said lyoslurry to form particles of encapsulated probiotic bacteria; and
   (e) packaging said encapsulated probiotic bacteria in an air-tight container.

2. The process of claim 1, wherein lyophilising is performed at about −50° C. for about 30 to about 36 hours.

3. The process of claim 1, whereby said encapsulated probiotic bacteria is stable in simulated gastric fluid (SGF) for up to 6 hours.

4. The process of claim 1, whereby when the encapsulated probiotic bacteria is contacted with simulated intestinal fluid (SIF) the bacteria is released from the carboxymethyl cellulose sodium salt and maltodextrin in less than 1 hour.

5. The process of claim 1, whereby said encapsulated probiotic bacteria is more tolerant to acidic conditions of the stomach of monogastric animals as compared to unencapsulated probiotic bacteria.

6. The process of claim 1, wherein providing the culture includes culturing *Bacillus amyloliquefaciens* or *Propionibacterium freudenreichii* in deMan-Rogosa-Sharpe liquid medium.

7. The process of claim 1, wherein the solution is mixed with the wet cake at a ratio of 1:1.

8. A monogastric animal feed supplement comprising the particles of encapsulated probiotic bacteria made by the process of claim 1.

9. The process of claim 1, wherein said particles of encapsulated probiotic bacteria have a moisture content of not more than 5% by weight.

* * * * *